United States Patent [19]
Yelderman et al.

[11] Patent Number: 5,095,913
[45] Date of Patent: Mar. 17, 1992

[54] SHUTTERLESS OPTICALLY STABILIZED CAPNOGRAPH

[75] Inventors: Mark Yelderman, Plano, Tex.; Daniel S. Goldberger, San Francisco; James R. Braig, Oakland, both of Calif.

[73] Assignee: Critikon, Inc., Tampa, Fla.

[21] Appl. No.: 522,208

[22] Filed: May 11, 1990

Related U.S. Application Data

[63] Continuation-in-part of Ser. No. 401,952, Sep. 1, 1989, abandoned.

[51] Int. Cl.$^5$ .............................................. A61B 5/00
[52] U.S. Cl. .................................. 128/719; 128/633; 128/664; 250/339; 250/343; 250/345
[58] Field of Search .............. 128/633, 664, 716, 719; 250/339, 343, 345; 422/84; 436/900; 73/23.3, 23.37; 356/435–439; 374/133, 181

[56] References Cited

U.S. PATENT DOCUMENTS

| | | | |
|---|---|---|---|
| Re. 19,564 | 5/1935 | Quereau | 374/133 |
| 3,539,804 | 11/1970 | Billetdeaux et al. | 250/43.5 |
| 3,745,349 | 7/1973 | Liston | 250/218 |
| 3,987,303 | 10/1976 | Stoft et al. | 250/343 |
| 4,423,739 | 1/1984 | Passaro et al. | 128/719 |
| 4,648,396 | 3/1987 | Raemer | 128/204.22 |
| 4,722,612 | 2/1988 | Junkert et al. | 374/124 |
| 4,727,886 | 3/1988 | Conrardy et al. | 128/725 |
| 4,772,790 | 9/1988 | Aldridge | 250/343 |
| 4,817,013 | 3/1989 | Corenman et al. | 364/497 |
| 4,827,938 | 5/1989 | Parker | 128/633 |
| 4,829,183 | 6/1989 | McClatchie et al. | 250/346 |
| 4,859,859 | 8/1989 | Knodle et al. | 250/504 R |
| 4,914,719 | 4/1990 | Conlon et al. | 250/339 |

OTHER PUBLICATIONS

"A Reliable, Accurate CO$_2$ Analyzer For Medical Use", Rodney J. Solomon, Hewlett-Packard Journal, Sep. 1981, pp. 3-21.
Model DR46 Dual Element Thermopile Detector, Technical Description, Dexter Research Center, Mar. 1985.
"Infrared Gas Analysis & Instrumentation", *Cascadia Technology Corporation*, Redmond, WA.
"Thermopile Detectors", *Northwoods Technologies, Inc.*, Crystal Fall, MI.
"Model 1M Thermopile Detector", *Dexter Research Center, Inc.*, Dexter, MI.

*Primary Examiner*—Kyle L. Howell
*Assistant Examiner*—Kevin Pontius
*Attorney, Agent, or Firm*—Woodcock, Washburn, Kurtz, Mackiewicz & Norris

[57] ABSTRACT

Methods and apparatus for constructing optically stabilized, shutterless infrared capnographs are disclosed. The capnographs of the present invention provide the absolute concentration of the constituents of the respiratory airstream of a patient, without the thermal drift problems normally associated with thermopile detectors, thereby providing a device with a high degree of accuracy. The present invention eliminates the need for a mechanical shutter to modulate the incident infrared beam and the need for a modulated source, thereby increasing the reliability and response time of the devices disclosed. Capnographs which are substantially unaffected by changes in the ambient temperature at which they operate are provided by connecting pairs of optically filtered thermopiles in series and processing the resulting differential pair.

47 Claims, 4 Drawing Sheets

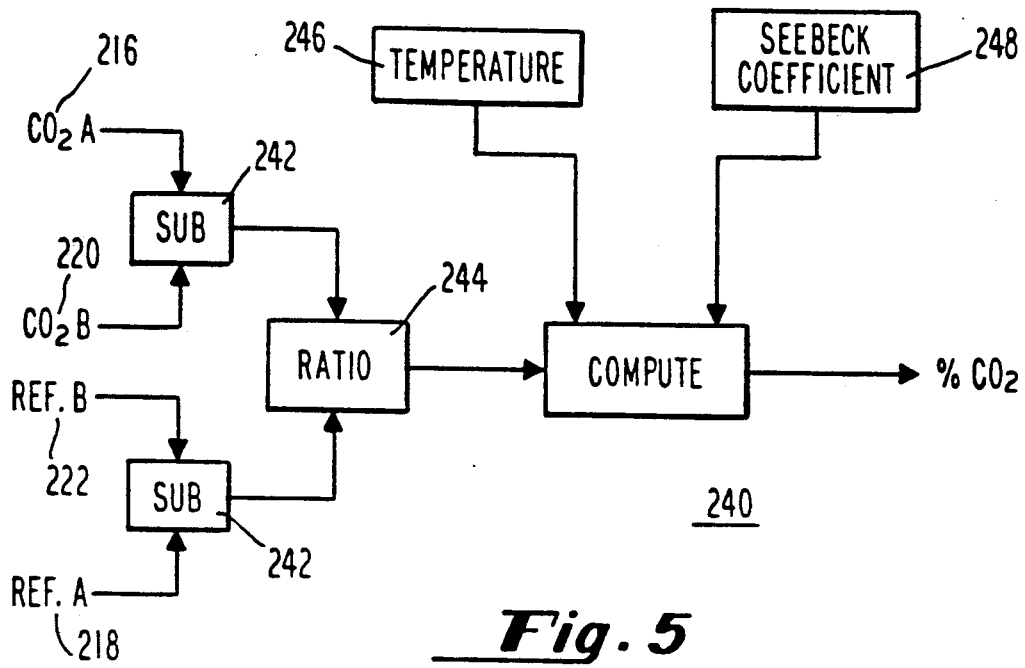
Fig. 5
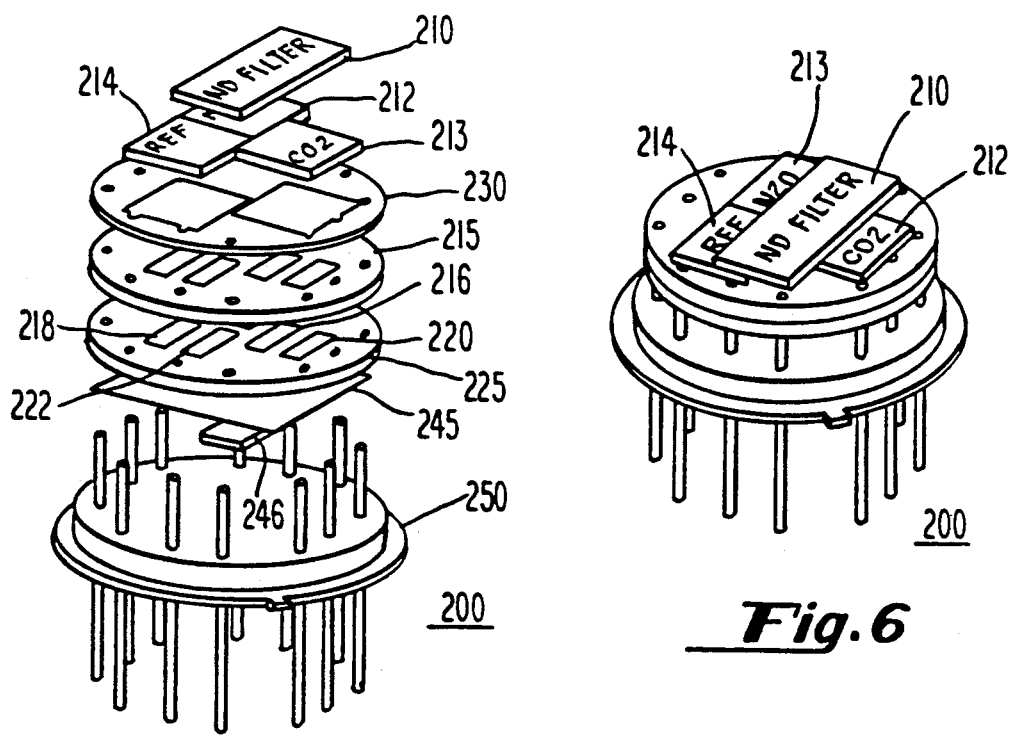
Fig. 7
Fig. 6

SHUTTERLESS OPTICALLY STABILIZED CAPNOGRAPH

Cross-reference to Related Applications

This application is a continuation-in-part of our U.S. patent application Ser. No. 07/401,952, filed on Sept. 1, 1989, now abandoned.

BACKGROUND OF THE INVENTION

1. Field of the Invention

The present invention relates to methods and apparatus for continuously determining the concentration of the constituents of the respiratory gases of a patient. Most preferably, the apparatus of the present invention is employed to monitor the end tidal $CO_2$ and $N_2O$ concentrations of a patient.

2. Description of the Prior Art

It is frequently of critical importance to monitor the concentration of carbon dioxide ($CO_2$) in the gases inspired and expired from a patient under anesthesia, for expired $CO_2$ concentration is a reliable indicator of the carbon dioxide concentration in the arterial blood. In a clinical setting, monitoring expired $CO_2$ prevents malfunctions in anesthesia rebreathing apparatus from going undetected and delivering excessive amounts of $CO_2$ to the patient. Rebreathing of anesthetic gases is very cost effective and environmentally desirable, but accurate $CO_2$ concentrations are difficult to maintain in the patient circuit without a concentration monitor.

It is known that by directing infrared radiation through a sample of a gaseous mixture and measuring the incident radiation illuminating a detecting device, a measure of the infrared absorption of the gas can be obtained. Electrical signals produced by a detecting device in such a manner are thus indicative of the infrared absorption of the gas and can be processed to produce an output indicating the concentration of one or more of the constituents of the gas being analyzed. This type of gas analyzer operates on the principle that various gases exhibit substantially increased absorption characteristics at specific wavelengths in the infrared spectrum and that higher gas concentrations exhibit proportionally greater absorption.

Prior art infrared gas analyzers such as that described in U.S. Pat. No. 4,648,396 to Raemer utilize thermopile detectors to analyze gas concentrations. A thermopile detector is comprised of a number of thermocouples. Thermal detectors such as thermopiles are used primarily for infrared sensing and respond to the total incident energy illuminating them. The number of thermocouples must be sufficient to develop enough voltage to develop a suitable signal to noise ratio. A thermistor is used to calculate the Seebeck coefficient, which relates the voltage developed by the thermopile to the temperature differential between the "hot" and "cold" junctions of the thermopile. This coefficient is used to scale the output signal of the detector to indicate absolute gas concentration values.

Thermopile detectors as a class are known to suffer from thermal drift. Thermal drift causes a slow variation in the D.C. voltage output of the detectors and leads to measurement inaccuracies. Raemer overcomes this problem by using A.C. coupling between the thermopiles. This solution to the thermal drift problem, however, renders the resulting analyzer incapable of measuring absolute, steady state, gas concentrations. Instead, such devices are merely able to respond to changes in the concentrations of the gases being measured.

One method which attempts to obtain absolute gas concentrations involves modulating, or "chopping+, the incident energy beam. This technique is taught in U.S. Pat. No. 4,423,739 to Passaro. In order to accomplish the required modulation, mechanical means such as a chopper are frequently employed. The resulting analyzer is large, and is thus subject to failure as the moving parts of the beam modulation apparatus wear. Such failure may have catastrophic consequences rendering the analyzer inoperable.

An alternative method of modulating an energy beam is to construct a modulated source. Devices of this type are disclosed in U.S. Pat. No. 3,745,349 to Liston, for example. However, to date, analyzers employing modulated sources have suffered from slow response times due to the relatively long period required for the infrared emissions to decay after the excitation power is removed. Another shortcoming of modulated sources, familiar to those skilled in the art, is the relative instability of their energy output.

In addition, the imbalance between the excitation signals of two detectors has been utilized as a detection mechanism in the field of infrared motion detectors. In these devices, two detectors are arranged and their signals combined so that a null signal results when the detectors are identically excited. Any change in the environment that causes the output signal of one detector to change by an amount different than that of the other detector results in a non-zero differential signal. Thus, by subtracting the two output signals from two identical detectors an imbalance in the input excitation of the two detectors can be measured. An application of the method of subtracting two detector output signals, perhaps in an attempt to stabilize thermal drift, involves totally blocking one of the thermopile detectors with metal foil. This approach, however, is undesirable because of results in uneven heating of the substrate, thus causing an error signal to be introduced into the output.

Thus, at the present time, the devices available provide absolute concentrations with the trade-off of either decreased reliability in the case of mechanically shuttered devices, or slow response times in the case of modulated source devices. Eliminating either of these drawbacks using conventional thermopile detectors results in a device prone to inaccuracies due to thermal drift, or one incapable of determining absolute concentrations if the thermal drift is stabilized using A.C. techniques. Therefore, a reliable gas analyzer using thermopiles that is both immune to thermal drift and capable of providing absolute gas concentrations would be highly desirable.

SUMMARY OF THE INVENTION

It is an object of the present invention to provide methods and apparatus for detecting the absolute concentration of the constituents of a gas stream using thermopile detectors. Another object of the present invention is to eliminate the thermal drift from which thermopile detectors are known to suffer, while retaining the capability of measuring absolute gas concentrations.

It is a further object of the present invention to accomplish the above objects without modulating or "chopping" the incident energy beam.

Accordingly, the present invention provides a shutterless capnograph comprising an apparatus which has no moving parts, which does not require a modulated source of infrared radiation, and which does not suffer from thermal drift, thereby providing a device which overcomes the limitations of the prior art. The improvements provided by this invention are arrived at through a novel optical stabilization technique applied to thermopile detectors. A preferred embodiment of the invention provides a highly accurate, stable, reliable, lightweight and economical infrared capnograph which will permit increased clinical and diagnostic monitoring of the absolute concentrations of carbon dioxide, nitrous oxide or other gases present in the expired airstream of a patient.

The present invention provides apparatus comprising one or more channels of a shutterless infrared gas analyzer for detecting the concentration(s) of at least one gaseous component of a substantially gaseous flow stream. The apparatus comprises at least two infrared detectors which produce electrical signals when illuminated by optical energy and means for illuminating the detectors with infrared radiation. Means for directing at least a portion of the gas being analyzed between the detectors and the infrared source is provided along with means for attenuating the infrared energy illuminating at least one of the detectors and circuitry for combining the signals produced by the detectors to produce an optically stabilized signal. If desired, the apparatus may further comprise additional detectors, attenuators, and circuitry, sufficient to comprise separate channels of a multi-channel device. The apparatus may also function in conjunction with a host processor for storing, processing, and displaying the measured information.

As mentioned above, the drift usually associated with thermopile detectors is produced by a variation in the reference junction temperature. In normal construction, a thermopile detector is comprised of a series of thermocouple junction pairs. One element of each pair is attached to a substrate (typically ceramic) and called the reference junction while the other element is unattached, suspended over an opening, and is called the sensing element. Incident radiation illuminates the suspended sensing element and raises its temperature. A voltage develops that is related to the difference in temperature between the suspended and substrate attached elements. Drift arises, however, because the incident radiation and room temperature variations change the temperature of the reference junctions. The temperature differential between the sensing (hot) and reference (cold) junctions is thus altered; this condition in turn causes the output voltage to change, or drift.

A preferred embodiment of the present invention incorporates a substantially identical pair of thermopile detectors mounted on the same ceramic substrate and connected in series opposition. In this configuration, balanced and equal incident radiation illuminating the pair will produce no signal. Because the reference junctions of both detectors are on the same ceramic substrate and at substantially the same temperature, a drift in substrate temperature will produce no discernible change in output signal, thereby overcoming the above-mentioned problems. In order to make the system respond to incident radiation, an optical filter, or attenuator, with a transmission coefficient of approximately 0.50 (i.e., 50% transmission) is placed over one of the thermopile elements in the pair. With the filter in place the system responds to incident radiation but is substantially insensitive to other thermal changes. Also, in the present invention the output signals of the two thermopile detectors are subtracted. This is done not for the purpose of measuring any imbalance in the signals exciting the detectors, but rather to eliminate the effect of a variation in the background signals. For example, variations due to thermal drift are cancelled since they are common to both detectors.

The problem of uneven heating described above in connection with the method of blocking one of the detectors is eliminated in the present invention by utilizing attenuation filters that do not cause uneven heating of the substrate. These filters have known but different transmission coefficients so that the incident excitation signal can be accurately determined from the differential signal, as set forth in greater detail below.

In order to permit the analysis of specific gases, optical bandpass filters which permit the transmission of wavelengths within a specified bandwidth (i.e., that absorbed by the gas of interest) are disposed between the detectors and the gas directing means, thereby filtering the radiation prior to its striking the detectors. Since the center wavelength and bandwidth of optical filters vary with temperature, thermal drift should be considered when designing the optical bandpass filters. A preferred method for selecting the bandpass filters is described herein.

Circuitry for processing the signals produced by the detectors converts these signals into a ratio which is related to the absolute concentration of the gas constituent being measured. As a result, the capnograph of the present invention is substantially unaffected by changes in the ambient temperature of the environment in which it operates through the action of the neutral density filters. The technique described above for combining and processing the detector signals is referred to as "optical stabilization" herein.

A capnograph made in accordance with the present invention may further comprise additional pairs of thermopile detectors, attenuators, and optical bandpass filters, and such additional circuit means so as to form a multichannel device for determining the concentrations of more than one gas constituent. In such a multichannel embodiment, each of the channels has an optical filter permitting the transmission of radiation within the absorption bandwidth of the constituent being monitored.

A capnograph system made in accordance with the present invention may also have a host system for collecting and processing data collected by the detectors. Such a capnograph system may also include a device for indicating the absolute concentration of the constituent or constituents being monitored, thus providing the necessary concentration information in a usable form.

A preferred infrared energy detector for use in a capnograph made in accordance with the present invention is also disclosed. The detector uses paired thermopiles preceded by an analytical or reference bandpass filter, with a neutral density filter also placed in the optical path of one detector in the pair. This, two channels—one analytical and one reference—are preferably provided to permit measurements to be taken while the background effects are cancelled.

Most preferably a capnograph made in accordance with the present invention will be used to determine the absolute concentrations of carbon dioxide and/or nitrous oxide in the inspired and expired airstream of a patient. However, the optically stabilized detectors disclosed need not be so limited, and may be utilized to determine the concentrations of any of a number of constituents, as will be apparent to one skilled in the art from the following description.

BRIEF DESCRIPTION OF THE DRAWINGS

FIG. 5 is a schematic representation of the processing performed on the signal detected by the apparatus of FIG. 4;

FIG. 6 is a perspective view of a detector constructed in accordance with the schematic illustration of FIG. 4; and FIG. 7 is an exploded view of the detector of FIG. 6.

DETAILED DESCRIPTION OF THE PREFERRED EMBODIMENTS

A. Optically Stabilized Thermopile Detector

Figure 1:
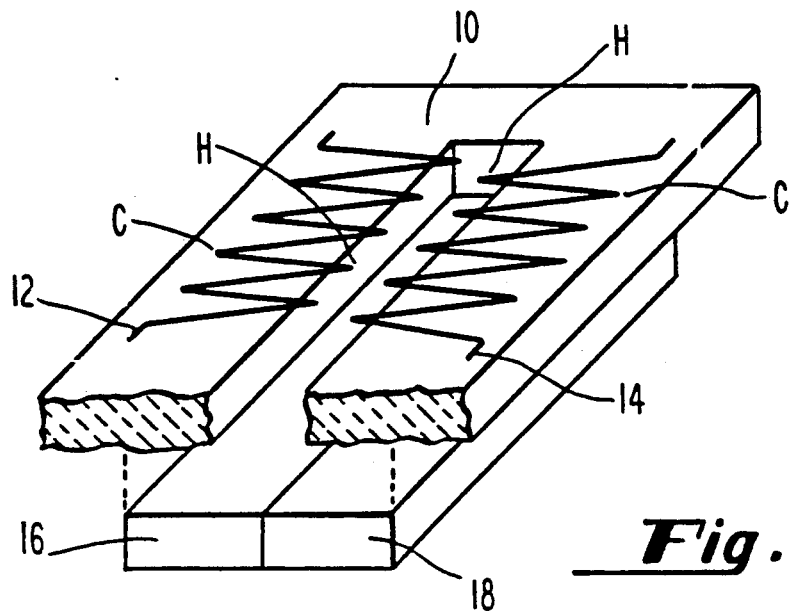
FIG. 1 is a foreshortened isometric view of the thermopile detector assembly of the present invention.

FIG. 1 depicts a typical thermopile detector construction. It can be seen that such a thermopile detector is a group of thermocouples connected in series. The present invention utilizes a first set of thermocouples, comprising a first thermopile 12, and a second set of thermocouples, comprising a second thermopile 14, both preferably mounted on a common ceramic substrate 10, as shown. The hot, or sensor, junctions of the thermocouples are typically denoted H, while the cold, or reference, junctions are denoted C. Most preferably, the thermocouples 12 and 14 are the type comprising a metallic circuit deposited upon a polyester film, such as Mylar, or other suitable substrate. A preferred embodiment utilizes thermocouples having a substrate thickness of 1 mil.

Also shown in FIG. 1 is the placement of neutral density (attenuation) filters 16 and 18, each of which has a different transmission coefficient. Typically, filter 16 has a transmission coefficient of 1.00 and filter 18 a transmission coefficient of 0.50.

In a preferred embodiment, detector 12 is electrically connected to detector 14 in series opposition. The resulting difference signal will only be indicative of the incident radiation. Signals caused by substrate temperature changes will cancel, provided the temperature is uniform across the substrate. discussed more fully in the mathematical derivation provided below.

Thus, in a preferred embodiment, the thermopile detectors 12 and 14 are "optically stabilized". This design overcomes the requirement for source modulation described above by rendering the detector substantially immune to thermal drift. Since each of the thermopile detectors 12 and 14 is exposed to the same incident energy beam but has different attenuation filters 16 and 18 in line with that energy, the differential signal from the two detectors is therefore related only to the incident energy and the transmission coefficients of the neutral density attenuation filters. The stabilization technique disclosed by the present invention is useful with a variety of detectors, such as the Model DR34 manufactured by Dexter Research Inc., Ann Arbor, Mich. Moreover, since the optically stabilized detectors of the present invention are sensitive to a wide range of wavelengths, and are relatively inexpensive and rugged, they can be beneficially used in a shutterless infrared capnograph for monitoring respiratory gas.

Figure 4:
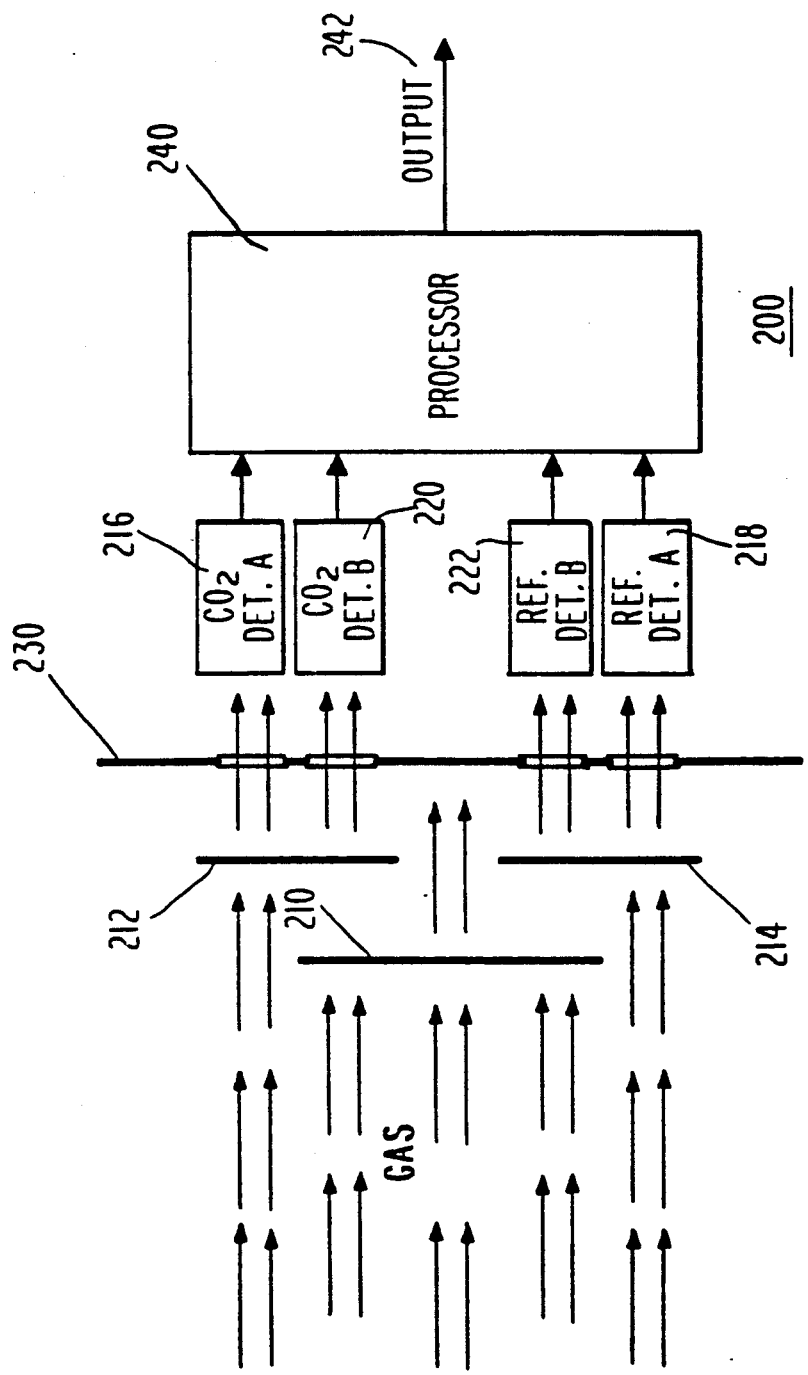
FIG. 4 is a schematic illustration of a detector and its optical path, constructed in accordance with the principles of the present invention.

In FIG. 4, the optical path of an embodiment of a detector 200 constructed in accordance with the principles of the present invention is shown. Infrared energy is emitted from an IR source 300 and passes through the gas being analyzed, which in this example is $CO_2$. Some of the infrared energy is absorbed by the gas in front of the IR source 300, and the remainder of the infrared energy impinges upon a group of filters, including a neutral density filter 210, an analytical $CO_2$ filter 212, and a reference filter 214. The neutral density filter 210 uniformly attenuates all wavelengths of energy which are incident upon the filter. The analytical $CO_2$ filter 212 is a bandpass filter which passes a narrow band of energy, including those wavelengths absorbed by $CO_2$. The reference filter 214 is also a bandpass filter which passes a band of energy excluding those wavelengths absorbed by $CO_2$.

It is seen that the neutral density filter 210 overlaps or shadows the subsequent analytical and reference filters 212 and 214, as well as two of the thermopile detectors 216 and 218, $CO_2$ detector B 220 and reference detector B 222. Thus, each detector A 216 and 218 will receive energy which has been transmitted by its respective analytical filter 212 or reference filter 214, but not the neutral density filter 210. Each detector B 220 and 222, on the other hand, receives energy passed by its respective analytical filter 212 or reference filter 214 as well as the neutral density filter 210. Following the filters is an aperture or window 230 which transmits energy to only the detector areas of the substrate on which the detectors are formed. The outputs of the detectors are passed to a processor 240 for the production of an output signal 242 representative of the concentration of $CO_2$ in the gas being analyzed.

A main purpose of the neutral density filter 210 is to provide signals which allow the desired signal to be distinguished from signal interference such as background (local thermal) effects. A number of attempts have been made in the prior art to deal with these effects. For instance, U.S. Pat. No. 4,772,790 to Aldridge attempts to isolate these effects by using ten thermopiles for each detector channel, with only a central portion of the area of the thermopiles being used to develop a usable signal. In addition, U.S. Pat. No. 3,539,804 to Billetdeaux et al. attempts to deal with the problem through heating and shielding of the detector, and also includes a rotatable neutral attenuator as a zeroing mechanism in assembly balancing of a $CO_2$ detector. By contrast, in an embodiment of the present invention, local thermal effects are eliminated by developing signals resulting in their cancellation when the signals are combined.

For instance, an examination of the $CO_2$ channel reveals that the $CO_2$ detectors A 216 and B 220 are in close proximity to each other and hence experience similar effects from background and other local radiation sources. Each detector produces an output signal containing a component I, the desired incident infrared signal, and a component b due to background effects. Absent the presence of the neutral density filter 210, the CO₂ detectors 216 and 220 would produce signals of the form:

$$Det. \ A = R(I_a + b), \text{ and}$$

$$Det. \ B = R(I_b + b),$$

where R is the response of the detectors.

It is desired to maximize the desired signal component I, which may be done by selecting a neutral density filter 210 which is about 100% transmissive at the absorption wavelength for CO₂. In this case A would equal B. The signal component I would be maximized but the difference of the two detector output signals would yield zero. Correspondingly, if the neutral density filter were chosen to be a 100% blocking filter (i.e., 0% transmissive, $I_b = 0$) at the absorption wavelength, their difference would be $A - B = RI_a$. This would have the undesirable effect of shadowing detector B 220 from all radiation from the IR source 300, thereby blocking detector B 220 from reception of incident energy, and would further set up an undesired thermal differential between the two detectors. Moreover, neither of these two choices leads to the ability to distinguish and eliminate background effects.

If, however, the neutral density filter 230 is chosen to have a transmissivity of about 50%, for instance, the desired incident energy component I would be differentiated and the background effects would substantially cancel. A neutral density filter of this character would produce signals of the form:

$$Det. \ A = R(I + b), \text{ and}$$

$$Det. \ B = R(0.5I + b).$$

Thus, when the difference of A minus B is taken, the result is 0.5 IR with the background effects b cancelling. Other transmissivity characteristics may be chosen in consideration of incident energy levels and the thermal effects of shadowing by the neutral density filter 210. For example, a 0% transmissive filter may be used.

The details of the processor 240 of FIG. 4 are shown in FIG. 5. The output signals of the A and B detectors 216 and 220 for the CO₂ and for the reference channels 218 and 222 are respectively subtracted at subtractors 242 to eliminate background radiation and substrate temperature effects, as explained immediately above. In a preferred embodiment of the present invention, this subtraction step 242 is accomplished by connecting the thermopile detectors in series opposition, so that the subtraction of their outputs is inherent in their interconnection as shown in FIG. 5. A ratio 244 is then taken of the incident signals after this cancellation of thermal effects. The ratio 244 of the analytical and reference signals eliminates proportionate effects of spurious absorption, such as those resulting from the accumulation of undesired particulate matter on the components of the detectors. For example, for an incident radiation signal having a normalized value of 0.8 CO₂ and filters which are contaminated with substances which absorb some of the radiation being measured, the transmissivity of the optical paths is reduced to 0.9 of full transmissivity. The output signal would thus be the product of these losses, or 0.72 CO₂. When the reference channel is subject to the same contamination, which may be substantially achieved by close proximity of the detectors and filters, the same factor of 0.9 would be present in signals of the reference channel. Hence, the ratio of the CO₂ and reference signals would contain the 0.9 factor in both the numerator and the denominator for a ratio of one, eliminating the effects of contamination.

Computations are made on the calculated ratio to further refine the measurement of CO₂. The measurement of absolute substrate temperature, provided by the thermistor 246 in the detector, and the appropriate Seebeck coefficient 248 are factors taken into consideration in this computation. The temperature measurement is incorporated into the present invention as shown in the functional block diagram of FIG. 5. As will be understood by those of ordinary skill, the resultant measurement of CO₂ is obtained by solving the well-known Bier's Law equation which is of the form $I = I_o e^{-xac}$, where $I_o$ is a constant coefficient, x is path length, a is the absorption coefficient for CO₂, and c is concentration. The reference channel yields a value for I, since the absorption coefficient and concentration of CO₂ in the reference channel are zero by reason of the elimination of CO₂ wavelengths from the reference filter passband. The detector output signal supplies the value for I, and the equation is solved for c, the concentration of CO₂ in the gas being measured. The above computations are preferably performed by a host processing system of the type described below with respect to FIG. 3.

In a preferred embodiment, a second analytical channel is employed for N₂O. This channel is identical to the CO₂ channel in FIG. 4, except that the analytical filter 212 is chosen to pass wavelengths representative of the absorption of infrared energy by N₂O instead of CO₂. The outputs of the A and B detectors for the N₂O channel are combined to eliminate background and substrate thermal effects and the reference channel outputs are combined to yield a measurement of N₂O concentration, as in the CO₂ computation set forth immediately above. In addition, such N₂O concentrations may be used in accordance with the techniques taught by Severinghaus, M. D., Larson, M. D. and Eger, M. D. in an article entitled "Correction Factors for Infrared Carbon Dioxide Pressure Broadening by Nitrogen, Nitrous Oxide and Cyclopropane" in *Anesthesiology*, May-June, 1961, pp. 429–432, to correct for collision broadening errors induced in the CO₂ gas concentration computation by nitrous oxide.

FIGS. 6 and 7 respectively illustrate in perspective assembled and exploded views a detector constructed in accordance with the present invention. The detector 200 employs the same principles and optical paths shown in FIG. 4. As shown in the perspective of the assembled detector 200 shown in FIG. 7, the neutral density filter 210 is disposed above the reference filter 214 and the analytical filters 212 and 213. In the embodiment of the present invention shown, analytical filters 212 and 213 selected to analyze CO₂ and N₂O are provided, as well as the reference filter 214. Each of these three filters is "shadowed" or blocked by the neutral density filter 210 as explained above with reference to FIG. 4.

Further details of the construction of the detector are shown in the exploded view of the infrared detector 200 in FIG. 7. Beneath the filters 210, 212, 213, 214 is the filter aperture 230. The thin film thermopile detectors 216, 218, 220 and 222 are sandwiched between two ceramic spacers 215 and 225.

In FIG. 7, the N₂O detectors 224 and 226 are not visible. A foil background 245 is provided beneath the ceramic spacer/thermopile sandwich to block the further passage of the incident radiation, but it allows heat to be conducted through the device. Finally, beneath the foil background 245, a thermistor 246 is disposed which, as explained above, provides an absolute temperature indication. The above-mentioned components are mounted on a TO-8 12-pin header 250, as shown.

While the illustrated embodiments are shown to employ thermopile detectors, the principles of the present invention may also be applied through the use of other infrared detecting devices, such as thermistors, thermocouples, pyroelectric detectors, Golay cells, and PbSe photodetectors, for instance. However, the arrangement shown has the benefit that it is easy to manufacture, is small in size and light in weight.

B. Mathematical Derivation

The signal or voltage output, S, of a thermopile detector can be expressed as:

$$S = (T \cdot I \cdot R) + B,$$

where T is the filter transmission coefficient, assuming the filter is between the detector and the energy source, I represents the incident energy of the source, R is the responsivity of the detector, and B is the component of the signal attributed to background "noise", including room temperature and detector package temperature variations. In a preferred embodiment of the present invention, two detectors 12 and 14 are mounted on a common substrate 10 as shown in FIG. 1, creating a condition wherein the value of B for each detector is equal. The detectors 12 and 14 are used to simultaneously monitor an incident energy beam. Filters 16 and 18 having known but different transmission coefficients are placed between each detector 12 and 14 and the source of incident energy.

The two equations describing the outputs S1 and S2 of the two detectors 12 and 14 are combined and solved for I, yielding the following equation, which is independent of the value of B:

$$I = \frac{S_1 - S_2}{(T_1 \cdot R_1) - (T_2 \cdot R_2)}$$

In a most preferred embodiment, the numerator of the above equation, $S_1 - S_2$, which represents the difference signal, is computed by connecting the detectors 12 and 14 in series opposition. It should be apparent to one skilled in the art however, that the difference signal could be calculated using a digital computer or other electronic circuit. The equation demonstrates that the stabilization technique of the present invention eliminates the background effects term, B, from the final output of the circuit, thereby rendering a device substantially insensitive to room temperature effects.

C. Source Drift

Figure 2:
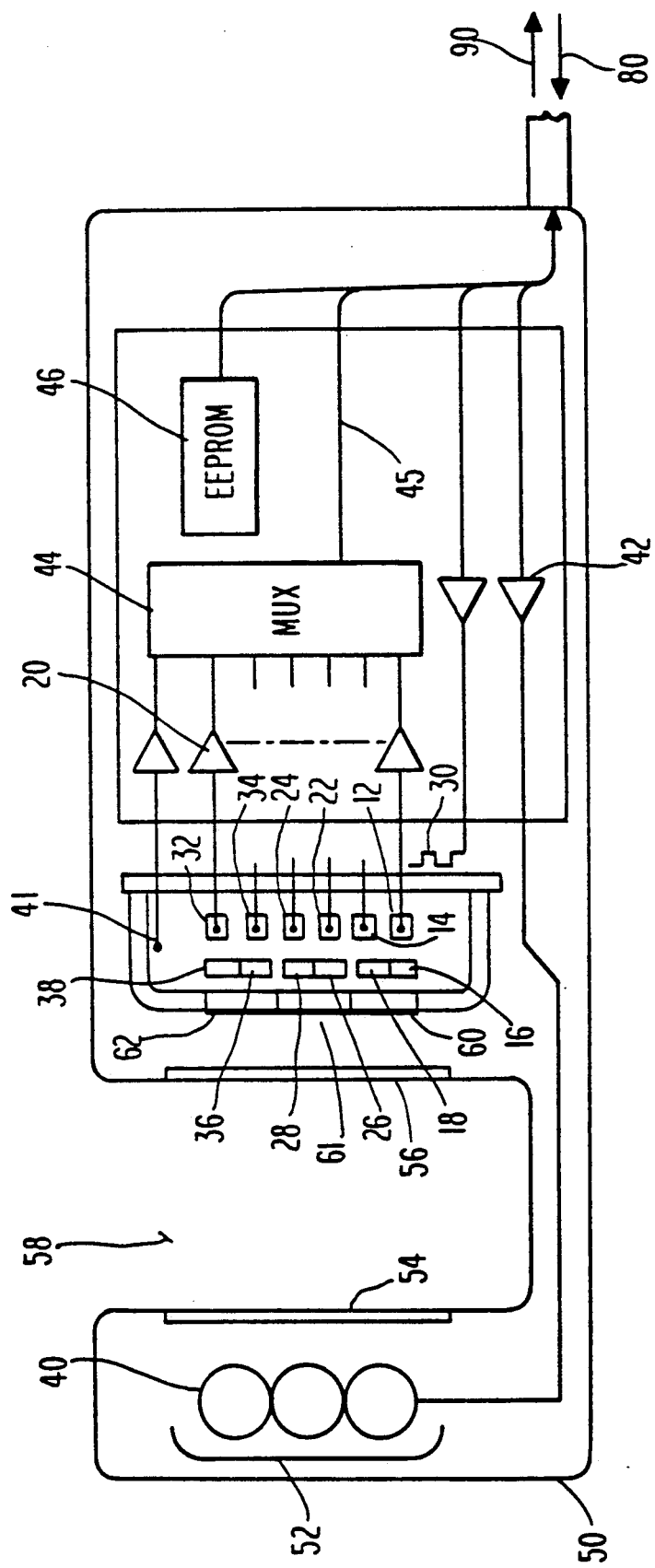
FIG. 2 is a partially schematic plan view of a gas analyzer and related circuitry, constructed in accordance with the present invention.

As will be understood by those having ordinary skill in the art, variations, or drift, in the infrared source may also cause drift in the output signals of the thermopile detectors 12, 14, 22, 24, 32 and 34 illustrated in FIG. 2. This drift may be eliminated by using two analytical filters, a first having its transmission at the absorption wavelength of the gas being analyzed, and a second designed to transmit some other unabsorbed wavelength. Energy in the unabsorbed band serves as a reference. This technique of referencing is well-known and is described in textbooks, see, e.g., Mullard Limited, *Applications of Infrared Detectors*, ISBN #901232 22X, Chapter 10, the pertinent portions of which are incorporated by reference as if fully set forth herein.

D. Optically Stabilized Gas Analyzer

A typical construction of a preferred embodiment of the present invention is illustrated in FIG. 2. The circuitry and other components which comprise the present invention will generally be assembled into a housing 50, appropriately configured to enable the various components to function as described below. Those of ordinary skill will be aware of the design parameters associated with the packaging of devices made in accordance with the present invention. Some of the considerations relevant to the design of the housing 50 are: external interface design, cooling requirements, shielding and isolation characteristics, size and weight, integration with a breathing tube, sample cell or other means of delivering a sample of the patient's expired air, and aesthetic and utility considerations.

An input signal 80 from a host processor or other source is transmitted through an analog hybrid 42, the signal from which excites a source of infrared radiation 40. A reflector 52 is provided to efficiently direct an incident beam of infrared radiation. The incident radiation passes through an optical window 54 and into the region of the gas stream to be analyzed 58. The gas stream itself may be contained in apparatus such as a clear tube or tube-like structure (not shown), which directs a portion of the gaseous flow through the measurement region 58. After the incident infrared radiation has passed through the gas stream, it will pass through another optical window 56, bandpass filters 60, 61 and 62 and neutral density attenuation filters 16, 18, 26, 28, 36 and 38 before finally reaching the thermopile detectors 12, 14, 22, 24, 32 and 34.

The embodiment pictured in FIG. 2 is designed to measure the concentration of two gases and may be denominated a three-channel detector, with one channel serving as a reference channel. As will be appreciated by those of ordinary skill, detectors may be constructed having anywhere from one to many channels, depending upon the number of constituent gases to be detected and analyzed. Thus, for example, in FIG. 2 in addition to detectors 12 and 14, second and third detector assemblies 22 and 24 and 32 and 34 are used to create three channels. Positioned above each detector assembly is a bandpass filter 60, 61 and 62, each channel employing a different bandpass filter. Thus, it is understood that a first channel comprises detectors 12 and 14, attenuation filters 16 and 18, and bandpass filter 60. A second channel comprises detectors 22 and 24, attenuation filters 26 and 28 and bandpass filter 61, and so forth.

The output signal for each channel, i.e., the difference signal described above, is passed through its respective amplifier 20 and transmitted to a multiplexer 44, which also receives a signal from a temperature sensor 41. The multiplexer 44 then outputs a detector signal 45, which is also combined with a signal from an electronically erasable programmable read only memory (EEPROM) device 46 to fashion an output signal 90. The Seebeck coefficient, described above, is stored in the EEPROM 46, and is used for scaling the detector signal 45 to indicate absolute gas concentration values.

Attenuation filters 16, 18, 26, 28, 36 and 38 are mounted directly on the ceramic substrate. Therefore, the output of the temperature sensor 41 will reflect the temperature of the attenuation filters as well as the reference junction temperature of the thermodetectors.

A heater 30 is also shown which may further regulate the temperature of the apparatus, if desired.

E. Bandpass Filters

The bandpass filters 60, 61 and 62 are placed an equal distance in front of their associated detectors, i.e., they are placed in a common plane, so that all three thermopile detectors have an equal field of view. Each filter is characterized by its center wavelength and half-power bandwidth. The conventional approach to specifying the bandpass filters would be to center the filters in the absorption band of interest and to make the bandwidth as wide as the absorption band. The present invention takes a different approach, however, than that of the prior art and utilizes bandpass filters having center wavelengths shifted away from the center of the absorption band and bandwidths wider than the absorption band. The method of specifying the bandpass filters in accordance with the present invention is described in more detail in the following section. The shifting and broadening of the bandpass filter minimizes cross-talk between channels and minimizes the effects of temperature variations and manufacturing tolerances on the filters.

For example, in a preferred embodiment of the invention one channel is used to detect $CO_2$, another channel is used to detect $N_2O$, and a third channel is used as a reference channel. The absorption band of $CO_2$ is centered at 4.256 microns, and the half-power wavelength is 0.180 microns. In a preferred embodiment of the present invention, however, the bandpass filter used for the $CO_2$ channel is centered at 4.2624 microns with a half-power bandwidth of 0.2088 microns. Due to manufacturing tolerances, the half-power wavelengths may vary by plus or minus 0.03 microns at the short wavelength edge, and plus 0.03 microns to minus 0.05 microns at the long wavelength edge.

The absorption band for $N_2O$ is centered at 4.5400 microns, with a bandwidth of 0.3 microns. For the reasons stated above, in a preferred embodiment the bandpass filter for the $N_2O$ channel has a center wavelength of 4.5397 microns and a bandwidth of 0.3190 microns. The short wavelength half-power point may by plus 0.01 microns to minus 0.03 microns. The long wavelength half-power point varies by plus or minus 0.03 microns.

The reference filter has a center wavelength of 4.8265 microns and a half-power bandwidth of 0.2088 microns. The short and long bandwidth edges may vary by plus or minus 0.03 microns. The bandwidth is designed to be as close as possible to the bandwidth of the $CO_2$ filter. This minimizes the thermal gradients across the substrate since the total energy passing through this filter will approximate the total energy passed by the $CO_2$ filter. The center wavelength is selected to be as close as possible to the center of the $CO_2$ and $N_2O$ bands, while at the same time maintaining isolation between those channels and the reference channel. Thus, this novel use of band shifting and widening, to minimize cross-talk and the effects of thermal shift and manufacturing tolerances, in the design of the bandpass filters 60, 61 and 62 is integral to carrying out the preferred embodiment.

1. Analytical Bandpass Filter Specification

This section describes a method for specifying bandpass filters for a preferred embodiment of an optically stabilized capnograph in accordance with the present invention. The following example describes the specification of bandpass filters employed by the $CO_2$, $NO_2$ and reference channels of a three channel analyzer. The method described does not deal with the construction of filters, but rather with a novel method of specifying bandpass filters for use in infrared gas analyzers, or capnographs.

a. Conventional Technique

From the prior art, a technique for specification of infrared bandpass filters can be summarized. The guidelines, or steps, can be stated as:

1. Specify a filter that has its center wavelength coinciding with the center wavelength of the gas intended to be analyzed. This is done to yield maximum specificity and minimum cross-talk.

2. Specify the half power bandwidth just wide enough to include all of the wavelengths absorbed by the gas of interest. This optimizes modulation, or the amount of energy, passed by the filter and absorbed by the gas.

In practice it is understood that filter center wavelengths change with temperature. This is shown at page 41 of the OCLI Infrared Handbook (1970) Optical Coating Laboratory Inc.

In the construction of gas analyzers incorporating filter designs engineers often overcome the filter shift by operating the filters in a temperature controlled environment. Such a design is taught by U.S. Pat. No. 4,423,739 to Passaro. This approach, however, is expensive and complicated. It is also recognized that manufacturing tolerances on infrared bandpass filters can result in a range of center wavelengths from a single production run. This is expressed as a ± tolerance of typically $\frac{1}{4}$% to 1% on the center wavelength. Accommodating this variation is often accomplished by calibrating each analyzer individually. This practice is also expensive.

In specifying $CO_2$ and $NO_2$ filters in accordance with the present invention, the first two steps consist of steps 1 and 2 of the conventional technique; i.e., conventional filters are specified. In the present example, gas spectra from SADTLER INDEX were used.

The resulting conventional filters are characterized by the following filter specifications, titled VER 1.2. They follow in written form and a graph which shows the filters as specified and as shifted by +.03 $\mu$, which is approximately 0.7%. It corresponds to the shift that would be produced by a rise in temperature of about 50° C. It also corresponds to the manufacturing tolerance specified. For reference, the spectra of $CO_2$ and $NO_2$ are also included on the graphs.

b. Analysis and Computer Performance Simulation

Following the drafting of the VER 1.2 specifications, a computer simulation technique was developed to test the validity of the design. A Perkin Elmer 1640 FTIR spectrophotometer (PE 1640) was used to measure the absorption spectra of the gases of interest, $CO_2$ and $N_2O$. The gases were at atmospheric pressure and in a 0.5 inch path length cell. 5.0% $CO_2$ and 50% $N_2O$ balance $O_2$ were used. The spectra data were transferred into a personal computer, with data reported every 0.1 $\mu$. These spectra were combined in a spreadsheet program with mathematical models of the filters. Modulation percentages were calculated by multiplying the gas spectra by the filter models and dividing the result by the product of the spectra and a 100% transmission model. Modulation, cross-talk, and effects of filter shifts were studied.

The results of this analysis will be discussed below in the section on performance comparison. The analysis showed that in order to meet the design goals of the project either individual calibration or temperature control of the filters, or both, would have to be specified. It was decided to optimize the filter specifications to avoid these complications.

c. Optimal Filter Specification

Next, the conventional filters were optimized by the following three steps:

3. The filter center wavelength was varied so as to minimize the modulation change as the filter shifts over 0.3 $\mu$.
4. The filter center wavelength and bandwidth were varied to minimize cross-talk.
5. The filter center wavelength and bandwidth were varied to minimize the change in cross-talk that occurred due to the filter shifting 0.3 $\mu$.

To provide a realistic shape to the simulated bandpass filter, the transmission of a real infrared bandpass filter was measured with the PE 1640. A data file was created which preserved the cut-on and cutoff edges of the real filter but replaced the middle section with a flat transmission of 80%. A program changed the width of the simulated filter by altering the width of the flat top to allow testing various filter bandwidths. The simulated filter was restricted to half-power bandwidths of greater than 0.1 $\mu$ to insure that the resulting optimized filter was manufacturable. With the gas spectra in memory and the adjustable ideal filter file prepared, a personal computer was programmed to sweep through all possible filter combinations for $CO_2$ and $N_2O$ filters and to select the best combination as indicated by:

1. Maximum modulation;
2. Minimum modulation Change over 0.3 $\mu$ filter shift,
3. Cross-talk modulation less than 0.7% for $CO_2$ (apx. 1 mmHg); and
4. Cross-talk modulation less than 1.0% for $N_2O$ (about 10 mmHg).

d. Performance and Comparison of VER 1.2 and VER 2.1 Filters i) Modulation

The optimized filter VER 2.1 has slightly less modulation than the conventional version.

|  | VER 1.2 | VER 2.1 |
|---|---|---|
|  | $CO_2$ CHANNEL | $CO_2$ CHANNEL |
| 5% $CO_2$ | 40.3% | 36.0% MODULATION |
|  | $N_2O$ CHANNEL | $N_2O$ CHANNEL |
| 50% $N_2O$ | 65.4% | 58.9% MODULATION |

This is due to the fact that both the VER 2.1 $CO_2$ and $N_2O$ filters are slightly narrower than the conventional VER 1.2 filters and not centered on the center of absorption for $CO_2$ and $N_2O$, respectively. This reduction is of little or no significance in the overall design of the analyzer.

(ii) Filter Shift Error

The sacrifice in modulation was offset by a much improved performance with respect to errors when the filters shift.

|  | NORMAL % MOD | SHIFTED % MOD | CHANGE % MOD | CHANGE mmHg |
|---|---|---|---|---|
|  | VER 1.2 | | | |
|  | $CO_2$ CHANNEL | | | |
| 5% $CO_2$ | 40.3 | 41.5 | 1.2 | 1.7 |
| 50% $N_2O$ | 0.2 | 0.3 | 0.1 | 0.1 |
|  | $N_2O$ CHANNEL | | | |
| 5% $CO_2$ | 0.8 | 0.7 | −0.1 | −1.0 |
| 50% $N_2O$ | 65.4 | 54.2 | −11.2 | −112.0 |
|  | VER 2.1 | | | |
|  | $CO_2$ CHANNEL | | | |
| 5% $CO_2$ | 36.0 | 36.3 | 0.3 | 0.4 |
| 50% $N_2O$ | 0.4 | 0.5 | 0.1 | 0.1 |
|  | $N_2O$ CHANNEL | | | |
| 5% $CO_2$ | 1.0 | 0.8 | −0.2 | −2.0 |
| 50% $N_2O$ | 58.9 | 56.3 | −2.6 | −26.0 |

The optimized filter specification reduced $CO_2$ error due to a shift of 0.3 $\mu$ reduced from 1.7 mmHg to 0.4 and the $N_2O$ error went from 112 to 26 mmHg.

(iii) Cross-talk

Cross-talk increased slightly from VER 1.2 to VER 2.1.

|  | CROSS-TALK ERROR | | | |
|---|---|---|---|---|
|  | VER 1.2 % MOD | mmHg | VER 2.1 % MOD | mmHg |
|  | $CO_2$ CHANNEL | | | |
| 50% $N_2O$ | 0.2 | 0.3 | 0.4 | 0.6 |
|  | $N_2O$ CHANNEL | | | |
| 5% $CO_2$ | 0.8 | 8.0 | 1.0 | 10.0 | e. Summary

The method yielded a filter set which is slightly different from that selected by conventional methods and, according to the simulations, better suited to yield a manufacturable gas analyzer with little or no individual adjustment. Preferred filter specifications are set forth in Table I below:

TABLE I

| INFRARED FILTER SPECIFICATIONS | |
|---|---|
| ALL FILTERS: | |
| Dimensions: | 0.187" × 0.156", +1− .003" 0.020", +1− .001" thick |
| Edge Irregularities: | <0.005" |
| Temperature Shift: | 0.01% per Deg. C. |
| Angle Shift: | 0.001% per Degree of angle. |
| Transmission at Center: | 80% |
| Cut-on - Cutoff Slopes: | 3% |
| Humidity Withstand per MIL-C-675A | |
| Abrasion Withstand per MIL-C-675A | |
| Coating Adherence per MIL-M-13508B | |

Spectral Characteristics below apply at 0 Deg. incidence and 30 Deg. C.

FILTER 1: Center 4.255 micron ±0.03 micron Half Power Bandwidth 0.180 micron ±1%

FILTER 2: Center 4.540 micron ±0.05 micron Half Power bandwidth 0.300 micron ±1%

FILTER 3: Center 3.600 micron ±0.03 micron Half Power Bandwidth 0.180 micron ±1%

F. Optically Stabilized Gas Analyzer Used With A Host Processor

Figure 3:
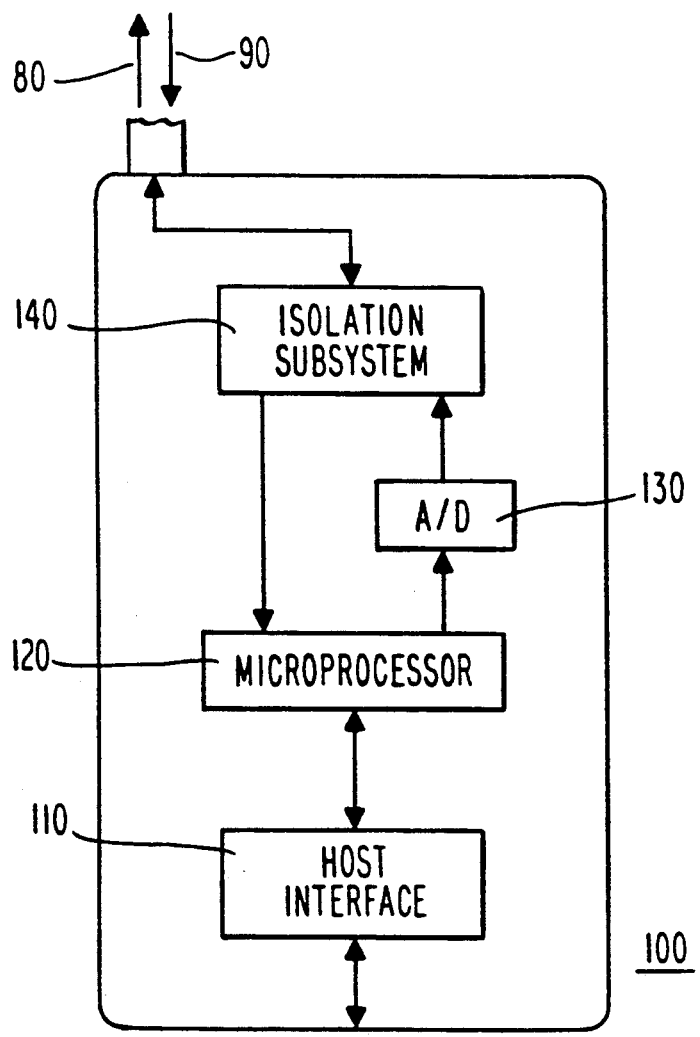
FIG. 3 is a schematic of further circuitry, illustrating the use of the present invention in conjunction with a host computer.

In FIG. 3 is illustrated a preferred embodiment of certain signal processing circuitry 100 used to carry out the present invention in conjunction with a host system. The input and output signals to the detector apparatus 80 and 90 are passed through an isolation and filtering subsystem 140 to insure patient safety. Output signal 90 of the detector flows through the isolation subsystem 140 to the AD converter detector 130, where it is digitized, before input into the microprocessor 120. Finally, the microprocessor 120 transmits the processed detector output—as a concentration value for the respective constituent gas—to the host system interface 110, and on to the host system (not shown). The final output signal may be monitored, recorded, stored, or further manipulated. Alternatively, a signal from the host system to the detector apparatus shown in FIG. 2 may be transmitted to the host system interface 110, then to the microprocessor 120, through the isolation and filtering subsystem 140, and finally on to the input 80 of the detector apparatus. The signal from the host system is not converted from digital to analog form before being input to the detector apparatus.

Although certain preferred embodiments of the present invention have been described herein, it should be understood that the invention is not so limited. Thus, many variations of the specific embodiments heretofore described are within the scope of the present invention as defined by the following claims.

What is claimed is:

1. A device for detecting the concentration of a gaseous component of a substantially gaseous flow stream, comprising:
   (a) a source of infrared radiation;
   (b) a pair of physically separate infrared detectors disposed on the same substrate so as to receive incident radiation from said infrared radiation source and to produce electrical signals representative of the received incident radiation;
   (c) means for directing at least a portion of said substantially gaseous flow stream between said detectors and said infrared radiation source;
   (d) attenuating means, disposed between only one of said detectors and said directing means, for attenuating the incident radiation impinging upon only said one detector; and
   (e) means for processing said electrical signals representative of the received incident radiation so as to produce an optically stabilized signal substantially unaffected by changes in the ambient temperature of the environment in which said device operates.

2. The device of claim 1, further comprising a pair of physically separate reference infrared detectors disposed on said substrate so as to receive incident radiation from said infrared radiation source which has passed through said substantially gaseous flow stream and to produce electrical signals representative of the received incident radiation, whereby said attenuating means is disposed between only one of said reference detectors and said directing means for attenuating the incident radiation impinging upon only said one reference detector.

3. The device of claim 2, further comprising a first optical filter disposed between said pair of infrared detectors and said directing means and a second optical filter disposed between said pair of reference infrared detectors and said directing means, said first optical filter passing a narrow band of energy about a wavelength readily absorbed by said gaseous component of said substantially gaseous flow stream and said second optical filter passing a band of energy excluding said wavelength readily absorbed by said gaseous component of said substantially gaseous flow stream.

4. The device of claim 3, wherein said processing means comprises means for determining the difference between electrical signals produced by said pair of infrared detectors and the difference between electrical signals produced by said pair of reference infrared detectors, means for determining a ratio between said differences, and means for computing from said ratio the concentration of said gaseous component of said substantially gaseous flow stream.

5. The device of claim 1, wherein said gaseous component is carbon dioxide.

6. The device of claim 1, wherein said gaseous component is nitrous oxide.

7. The device of claim 1, further comprising a housing having first and second optical windows constructed to permit the respective transmission of infrared radiation from said source through said first optical window, through said directing means, through said second optical window, and thereafter through said attenuating means before impinging upon said pair of infrared detectors.

8. The device of claim 1, further comprising an external processing system and an interface for interfacing inputs from said external processing system to said source so as to activate said source and for interfacing outputs of said processing means to said external processing system for further processing.

9. The device of claim 8, wherein said interface comprises a filter for isolating said external processing system from said device, an analog to digital converter for digitizing analog inputs from said external processing system, and a microprocessor for determining a concentration value for said gaseous component from said optically stabilized signal.

10. The device of claim 1, wherein aid attenuating means comprises an optical filter with a transmission coefficient of approximately 0.50.

11. The device of claim 1, wherein said pair of infrared detectors comprises a pair of thermopiles in opposed relation to each other.

12. A device for detecting the concentration of constituents of the respiratory airstream of a patient, comprising:
   (a) a source of infrared radiation;
   (b) a pair of physically separate infrared detectors, disposed on the same substrate so as to receive incident radiation from said infrared radiation source and to produce electrical signals representative of the received incident radiation;
   (c) means for directing at least a portion of said respiratory airstream of said patient between said detectors and said infrared radiation source;
   (d) attenuating means, disposed between only one of said detectors and said directing means, for attenuating the incident radiation impinging upon only said one detector; and
   (e) means for processing said electrical signals representative of the received incident radiation so as to produce an optically stabilized signal substantially unaffected by changes in the ambient temperature of the environment in which said device operates.

13. The device of claim 12, further comprising a pair of physically separate reference infrared detectors disposed on said substrate so as to receive incident radiation from said infrared radiation source which has passed through said respiratory airstream and to produce electrical signals representative of the received incident radiation, whereby said attenuating means is disposed between only one of said reference detectors and said directing means for attenuating the incident radiation impinging upon only said one reference detector.

14. The device of claim 13, further comprising a first optical filter disposed between said pair of infrared detectors and said directing means and a second optical filter disposed between said pair of reference infrared detectors and said directing means, said first optical filter passing a narrow band of energy about a wavelength readily absorbed by a constituent of the respiratory airstream of which its concentration is to be determined and aid second optical filter passing a band of energy excluding said wavelength readily absorbed by a constituent of the respiratory airstream of which its concentration is to be determined.

15. The device of claim 14, wherein said processing means comprises means for determining the difference between electrical signals produced by said pair of infrared detectors and the difference between electrical signals produced by said pair of reference infrared detectors, means for determining a ratio between said differences, and means for computing from said ratio the concentration of the constituent of the respiratory airstream whose concentration is to be determined.

16. The device of claim 12, wherein said one constituent is carbon dioxide.

17. The device of claim 12, wherein said one constituent is nitrous oxide.

18. The device of claim 12, further comprising a housing having first and second optical windows constructed to permit the respective transmission of infrared radiation from said source through said first optical window, through said directing means, through said second optical window, and thereafter through said attenuating means before impinging upon said pair of infrared detectors.

19. The device of claim 12, further comprising an external processing system and an interface for interfacing inputs from said external processing system to said source so as to activate said source and for interfacing outputs of said processing means to said external processing system for further processing.

20. The device of claim 19, wherein said interface comprises a filter for isolating said external processing system from said patient, an analog to digital converter for digitizing analog inputs from said external processing system, and a microprocessor for determining a concentration value for said at least one constituent from said optically stabilized signal.

21. The device of claim 12, wherein said attenuating means comprises an optical filter with a transmission coefficient of approximately 0.50.

22. The device of claim 12, wherein said pair of infrared detectors comprises a pair of thermopiles in opposed relation to each other.

23. A device for detecting the concentration of constituents of the respiratory airstream of a patient, comprising:
(a) a source of infrared radiation;
(b) a pair of physically separate infrared detectors for each constituent whose concentration is to be determined, said detectors being disposed on the same substrate so as to receive incident radiation from aid infrared radiation source and to produce electrical signals representative of the received incident radiation;
(c) means for directing at least a portion of said respiratory airstream of said patient between said detectors and said infrared radiation source;
(d) attenuating means, disposed between only one of said detectors in each pair and said directing means, for attenuating the incident radiation impinging upon only said one detector in each pair; and
(e) means for processing said electrical signals representative of the incident radiation received at each pair of detectors so as to produce optically stabilized signals substantially unaffected by changes in the ambient temperature of the environment in which said device operates.

24. The device of claim 23, further comprising a pair of physically separate reference infrared detectors disposed on said substrate so as to receive incident radiation from said infrared radiation source which has passed through said respirator airstream and to produce electrical signals representative of the received incident radiation, whereby said attenuating means is disposed between only one of said reference detectors and said directing means for attenuating the incident radiation impinging upon only said one reference detector.

25. The device of claim 24, further comprising optical filters disposed between each said pair of infrared detectors and said directing means and an optical filter disposed between said pair of reference infrared detectors and said directing means, said optical filters passing a narrow band of energy about a wavelength readily absorbed by the constituent of the respiratory airstream of which its concentration is to be measured by a corresponding pair of detectors and said optical filter passing a band of energy excluding said wavelengths readily absorbed by said constituents of the respiratory airstream of which their concentrations are to be determined.

26. The device of claim 25, wherein said processing means comprises means for determining first differences between electrical signals produced by respective pairs of infrared detectors and a second difference between electrical signals produced by said pair of reference infrared detectors, means for determining respective ratios between said first differences and said second difference, and means for computing from said ratios the concentrations of the constituents of the respiratory airstream whose concentrations are to be determined.

27. The device of claim 23, wherein said constituents are carbon dioxide and nitrous oxide.

28. The device of claim 23, further comprising a housing having first and second optical windows constructed to permit the respective transmission of infrared radiation from said source through said first optical window, through said directing means, through said second optical window, and thereafter through said attenuating means before impinging upon each of said pairs of infrared detectors.

29. The device of claim 23, further comprising an external processing system and an interface for interfacing inputs from said external processing system to said source so as to activate said source and for interfacing outputs of said processing means to said external processing system for further processing.

30. The device of claim 29, wherein said interface comprises a filter for isolating said external processing system from said patient, an analog to digital converter for digitizing analog inputs from said external processing system, and a microprocessor for determining concentration values for said constituents from said optically stabilized signals.

31. The device of claim 23, wherein said attenuating means comprises an optical filter with a transmission coefficient of approximately 0.50.

32. The device of claim 23, wherein said pair of infrared detectors comprises a pair of thermopiles in opposed relation to each other.

33. A shutterless infrared capnograph for detecting the concentration of constituents of the respiratory airstream of a patient, comprising:
 (a) a source of infrared radiation;
 (b) a pair of physically separate infrared detectors disposed on the same substrate so as to receive incident radiation from said infrared radiation source which has passed through said respiratory airstream and to produce electrical signals representative of the received incident radiation;
 (c) a pair of physically separate reference infrared detectors disposed on said substrate so as to receive incident radiation from said infrared radiation source which has passed through said respiratory airstream and to produce electrical signals representative of the received incident radiation;
 (d) means for directing at least a portion of said respiratory airstream of said patient between said detectors and said infrared radiation source;
 (e) attenuating means, disposed between only one of said detectors and said directing means and between only one of said reference detectors and said directing means, for attenuating the incident radiation impinging upon only said one detector and upon said one reference detector;
 (f) a first optical filter disposed between said pair of infrared detectors and said directing means for passing a narrow band of energy about a wavelength readily absorbed by a constituent of the respiratory airstream of which its concentration is to be determined;
 (g) a second optical filter disposed between said pair of reference infrared detectors and said directing means for passing a band of energy excluding said wavelength readily absorbed by a constituent of the respiratory airstream of which its concentration is to be determined; and
 (h) means for processing said electrical signals representative of the received incident radiation so as to produce an optically stabilized signal substantially unaffected by changes in the ambient temperature of the environment in which said device operates, said processing means comprising means for determining the difference between electrical signals produced by said pair of infrared detectors and the difference between electrical signals produced by said pair of reference infrared detectors, means for determining a ratio between said differences, and means for computing from said ratio the concentration of the constituent of the respiratory airstream whose concentration is to be determined.

34. The device of claim 33, wherein said one constituent is carbon dioxide.

35. The device of claim 33, wherein said one constituent is nitrous oxide.

36. A method of detecting the concentration of a gaseous component of a substantially gaseous flow stream, comprising the steps of:
 transmitting a beam of infrared radiation through said substantially gaseous flow stream;
 attenuating a portion of said infrared radiation which has passed through said substantially gaseous flow stream;
 detecting the intensity of said infrared radiation using a first detector and generating a first signal;
 detecting the intensity of only said attenuated portion of said infrared radiation using a second detector, physically separate from said first detector and disposed on the same substrate as said first detector, and generating a second signal;
 computing the difference between said first signal and said second signal and generating a difference signal; and
 processing said difference signal to produce an optically stabilized signal representative of the concentration of said gaseous component, whereby temperature gradients between said first and second detectors are prevented such that said optically stabilized signal is substantially unaffected by changes in the ambient temperature of the environment.

37. The method of claim 36, comprising the further step of filtering said infrared radiation and said attenuated portion of said infrared radiation through an optical filter which passes a narrow band of energy about a wavelength readily absorbed by said gaseous component of a substantially gaseous flow stream.

38. The method of claim 37, comprising the further steps of:
 filtering said infrared radiation and said attenuated portion of said infrared radiation through a blocking optical filter which passes a band of energy excluding said wavelength readily absorbed by said gaseous component of said substantially gaseous flow stream;
 detecting the intensity of the infrared radiation filtered by said blocking optical filter using a third detector disposed on said substrate and generating a third signal;
 detecting the intensity of the attenuated portion of the infrared radiation filtered by said blocking optical filter using a fourth detector, physically separate from said third detector and disposed on said substrate, and generating a fourth signal;
 computing the difference between said third signal and said fourth signal and generating another difference signal; and
 processing said difference signal with said another difference signal to determine said concentration of said gaseous component of said substantially gaseous flow stream.

39. The method of claim 38, wherein said step of processing said difference signals comprises the step of determining a ratio between said difference signal and said another difference signal.

40. A method of determining the concentration of a constituent of the respiratory airstream of a patient, comprising the steps of:
 transmitting a beam of infrared radiation through said respiratory airstream;
 attenuating a portion of said infrared radiation which has passed through said respiratory airstream;

filtering said infrared radiation and said attenuated infrared radiation through an optical filter which passes a narrow band of energy about a wavelength readily absorbed by said constituent of said respiratory airstream;

detecting the intensity of said filtered infrared radiation suing a first detector and generating a first signal;

detecting the intensity of only said filtered and attenuated infrared radiation using a second detector, physically separate from said first detector and disposed on the same substrate as said first detector, and generating a second signal;

computing the difference between said fist signal and said second signal and generating a difference signal; and processing said difference signal to determine said concentration of said constituent of said respiratory airstream of said patient substantially independent of changes in the ambient temperature of the environment.

41. The method of claim 40, comprising the further steps of:

filtering said infrared radiation and said attenuated infrared radiation through a blocking optical filter which passes a band of energy excluding said wavelength readily absorbed by said constituent of said respiratory airstream;

detecting the intensity of the infrared radiation filtered by said blocking optical filter using a third detector disposed on said substrate and generating a third signal;

detecting the intensity of the attenuated infrared radiation filtered by said blocking optical filter using a fourth detector, physically separate from said third detector and disposed on said substrate, and generating a fourth signal;

computing the difference between said third signal and said fourth signal and generating another difference signal; and processing said difference signal with said another difference signal to determine said concentration of said constituent of said respiratory airstream of said patient.

42. The method of claim 41, wherein said step of processing said difference signals comprises the step of determining a ratio between said difference signal and said another difference signal.

43. A method of monitoring the respiratory condition of a patient, comprising the steps of:

transmitting a beam of infrared radiation through a respiratory airstream of said patient;

attenuating a portion of said infrared radiation which has passed through said respiratory airstream;

filtering said infrared radiation and said attenuated infrared radiation through an optical filter which passes a narrow band of energy about a wavelength readily absorbed by a constituent of said respiratory airstream indicative of the respiratory condition of the patient;

detecting the intensity of said filtered infrared radiation using a first detector and generating a first signal;

detecting the intensity of only said filtered and attenuated infrared radiation using a second detector, physically separate from said first detector and disposed on the same substrate as said first detector, and generating a second signal;

computing the difference between said first signal and said second signal and generating a difference signal;

processing said difference signal to determine a concentration of said constituent of said respiratory airstream of the patient substantially independent of changes in the ambient temperature of the environment; and monitoring the concentration of said constituent of said respiratory airstream of the patient as an indicator of the respiratory condition of the patient.

44. The device of claim 1, wherein said substrate is a ceramic substrate and said pair of infrared detectors are disposed on physically separate portions of said substrate.

45. The device of claim 12, wherein said substrate is a ceramic substrate and said pair of infrared detectors are disposed on physically separate portions of said substrate.

46. The device of claim 23, wherein said substrate is a ceramic substrate and said pair of infrared detectors are disposed on physically separate portions of said substrate.

47. The device of claim 33, wherein said substrate is a ceramic substrate and said pair of infrared detectors and said pair of reference infrared detectors are disposed on physically separate portions of said substrate.

* * * * *

UNITED STATES PATENT AND TRADEMARK OFFICE
CERTIFICATE OF CORRECTION

PATENT NO. : 5,095,913

DATED : March 17, 1992

INVENTOR(S) : Yelderman et al.

It is certified that error appears in the above-identified patent and that said Letters Patent is hereby corrected as shown below:

Column 16, Claim 10, line 39, "aid" should be -- said --;

Column 17, Claim 14, line 17, "aid" should be -- said --;

Column 18, Claim 23, line 1, "aid" should be -- said --; and

Column 21, Claim 40, line 7, "suing" should be -- using --.

Signed and Sealed this

Twenty-eighth Day of December, 1993

*Attest:*

BRUCE LEHMAN

*Attesting Officer*    *Commissioner of Patents and Trademarks*